(12) United States Patent
Holtz et al.

(10) Patent No.: US 11,400,190 B2
(45) Date of Patent: Aug. 2, 2022

(54) VISIBLE VALVE SYSTEM AND SPILL REDUCING SYSTEM

(71) Applicant: MEDELA HOLDING AG, Baar (CH)

(72) Inventors: Raymond Holtz, Chicago, IL (US); Kathryn Mizuchi, Round Lake Beach, IL (US); Joseph Wach, Ingleside, IL (US)

(73) Assignee: MEDELA HOLDING AG, Baar (CH)

(*) Notice: Subject to any disclaimer, the term of this patent is extended or adjusted under 35 U.S.C. 154(b) by 231 days.

(21) Appl. No.: 15/040,216

(22) Filed: Feb. 10, 2016

(65) Prior Publication Data
US 2016/0228625 A1    Aug. 11, 2016

Related U.S. Application Data

(60) Provisional application No. 62/278,177, filed on Jan. 13, 2016, provisional application No. 62/114,436, filed on Feb. 10, 2015.

(51) Int. Cl.
*A61M 1/06* (2006.01)

(52) U.S. Cl.
CPC .............. *A61M 1/062* (2014.02); *A61M 1/06* (2013.01); *A61M 2205/21* (2013.01)

(58) Field of Classification Search
CPC .. A61M 2205/21; A61M 39/22; A61M 39/24; A61M 2039/2433; A61M 2005/3128; A61M 39/06; A61M 2039/0633; A61M 1/062; A61M 1/00; A61M 1/0049; A61M 1/06–1/0697
See application file for complete search history.

(56) References Cited

U.S. PATENT DOCUMENTS

| | | | |
|---|---|---|---|
| 4,673,388 A | 6/1987 | Schlensog et al. | |
| 6,090,065 A | 7/2000 | Giles | |
| 6,673,036 B1* | 1/2004 | Britto | A61M 1/06 604/346 |
| 2007/0179439 A1* | 8/2007 | Vogelin | F16K 15/144 604/74 |
| 2008/0208116 A1 | 8/2008 | Dao et al. | |
| 2011/0301532 A1 | 12/2011 | Wach et al. | |

OTHER PUBLICATIONS

International Search Report and Written Opinion, International Application No. PCT/IB2016/000209, dated Aug. 9, 2016.
Communication Relating to the Results of the Partial International Search, International Application No. PCT/IB2016/000209, dated May 30, 2016.
Chinese Patent Application No. 201680014290.2, Notification of First Office Action, dated Jul. 24, 2019.
Chinese Patent Application No. 201680014290.2, Notification of Second Office Action, dated Nov. 25, 2019.

* cited by examiner

*Primary Examiner* — Brandy S Lee
*Assistant Examiner* — Hong-Van N Trinh
(74) *Attorney, Agent, or Firm* — Marshall, Gerstein & Borun LLP (57) ABSTRACT

A visible valve system for a breastmilk expression system is set forth. The visible valve system includes an outer member, graspable by a human hand. The outer member provides a visual indication that the system is properly assembled. The visible valve system can reduce spillage from a breastmilk container by providing at least a portion of a spill reducing tortuous path in the system, or the spill-reducing tortuous path may be provided in another component of a breastmilk expression system of which the visible valve system is a part.

7 Claims, 6 Drawing Sheets

VISIBLE VALVE SYSTEM AND SPILL REDUCING SYSTEM

CROSS-REFERENCE TO RELATED APPLICATIONS

This application claims the benefit of the filing date of U.S. Provisional Patent Application No. 62/114,436, filed Feb. 10, 2015, and U.S. Provisional Patent Application No. 62/278,177, filed Jan. 13, 2016. U.S. Provisional Patent Application No. 62/114,436 and U.S. Provisional Patent Application No. 62/278,177 are hereby incorporated by reference.

FIELD OF THE DISCLOSURE

The present disclosure relates generally to breastmilk expression systems and, more particularly, to breastmilk expression systems including a spill reducing system. The spill reducing system can be partially or fully incorporated into a visible valve system for facilitating media flow from a conduit to a container, such as a bottle, a bag, or other suitable receptacle.

BACKGROUND

Nursing mothers, and in particular first-time nursing mothers, face a number of distractions and challenges associated with successfully nursing their babies. Breast pumps can be used by mothers to generate breastmilk for feeding their babies at a later time. While various breast pumps have provided nursing mothers with the ability to pump breastmilk for later feedings, kits that mothers connect to breast pumps have a number of small parts that can become lost, or that the nursing mothers may simply forget to properly assemble. One small part that can easily become lost from a kit is a valve that is commonly used to provide media communication from a conduit to a container for collecting the breastmilk. Additionally, even when the valve is in place in the kit, the kit can tip over during a pumping session causing the breastmilk to spill out of the container.

SUMMARY OF THE DISCLOSURE

In accordance with the principles of the present disclosure a spill reducing breastshield assembly for a breastmilk expression system is set forth. The breastshield assembly is configured to attach to a container, and can include a removable, visible valve system. The visible valve system is not only easily assembled by the user, but also provides a visible indication to the user that the system is properly assembled. As the term "visible valve system" is used herein, it refers to a valve assembly of a breastmilk expression system that has an external portion, or outer member, which is directly visible (i.e., not through some other component such as a collection container) by a user from an exterior of the breastmilk expression system when assembled, and during pumping and milk collection, even if a valve mechanism, or inner valve member, of which may not be visible in that configuration. The visible valve system is a visible component that can easily be correctly assembled within the breastmilk expression system to serve its intended purpose. Additionally, the visible valve system can serve as a spill reducing system, or a component of a spill reducing system for the breastmilk expression system. Alternatively, the spill reducing system can be incorporated elsewhere in a breastmilk expression system.

Various exemplary visible valve systems are disclosed herein that are suitable for use with breastmilk expression systems, although numerous variations of the embodiments and other embodiments are contemplated in accordance with the principles of the present disclosure. For example, in one exemplary spill reducing breastshield assembly for a breastmilk expression system, the breastshield assembly is configured to attach to a container, and can include a breast interface, such as a funnel-shaped breastshield. The breast shield can be removably securable to a breastshield mount, or conduit, that cooperates with such other components as a cap and a suitable container for collecting breastmilk.

Any suitable connection can be formed between the conduit and the visible valve system. In one exemplary embodiment, the conduit may be provided with one or more plug elements, each of which can be received in one or more slots of the visible valve system, if desired. For example, where the conduit includes threaded plug elements, the container for collecting breastmilk can include thread segments that cooperate with the threaded plug element(s) of the conduit when the threaded plug elements are selectively seated within the visible valve to threadedly engage a threaded region of the container.

In an embodiment, the conduit may include a breastmilk-receiving cavity, or media separation well, at least partially defined by a valve seat. An opening is provided in the valve seat. The opening can be closed by a valve member when sufficient negative pressure is applied to the system to extract breastmilk, which milk is temporarily collected in the media separation well. The valve can be preloaded so as to be biased in a closed condition, i.e. in sealing engagement with the valve seat. The media separation well can direct media flow through the conduit when the breastmilk expression system is fully assembled with the visible valve system, and in use. When the system pressure undergoes certain changes in conditions, the valve member opens, permitting breastmilk in the media separation well to pass through the opening and into the container.

The visible valve system can be a one piece (i.e., integral) component of a breastmilk expression system and can include an outer member and an inner valve member. The inner valve member can be connected to, or integrally formed with, the outer member. The visible valve system can be configured to detachably fit, either directly or indirectly, an attachment or docking portion of each of the container and the conduit. The visible valve system may be disposed intermediate the conduit and the container. As a result, the inner valve member can be assembled and removed from the system without the user needing to handle, or make any physical contact with, the inner valve. Further, by forming the inner valve integrally in the valve system, the entire valve system is easy to clean, and the likelihood that the inner valve member alone will become misplaced or forgotten when assembling the breastmilk expression system is eliminated.

The visible valve system can include at least one vent between the outer member and the inner valve member. The vent may vent air from the container to the atmosphere, or provide a portion of a channel that vents air from the container to the atmosphere. The visible valve system may further be provided with structural elements that form all or a portion of a spill reducing tortuous path for breastmilk. The spill reducing tortuous path can reduce spillage of breastmilk during use of the spill reducing breastshield assembly for a breastmilk expression system. The spill reducing tortuous path can be formed by connecting the visible valve system to the breastmilk expression system, and any suitable variation in the configuration of the visible valve system or conduit can be made to achieve the spill reducing tortious path upon assembly. The spill reducing tortuous path can include any structure that creates increased resistance to flow in the system, such as by bending, redirecting, or otherwise creating back pressure to limit liquid flow from a container connected to the visible valve system through the path.

Alternatively, a spill reducing tortuous path can be formed elsewhere in the breastmilk expression system, with or without inclusion of the visible valve system. For example, the spill reducing tortuous path can be formed in the conduit, container, or in a separate component adapted to be fitted to the breastmilk expression system.

When the spill reducing tortuous path is provided wholly or in part by a visible valve system constructed in accordance with the principles herein, the path can be provided in a variety of configurations to redirect media flow from the container. For example, the visible valve system can include a series of incomplete annular ribs that project from the visible valve system, with gaps of adjacent incomplete annular ribs offset from one another, such as by a center-to-center separation of some distance or, in the case of a round visible valve system, by one or more varied angles, thereby defining a spill reducing tortuous path to limit leakage, in the event the breastmilk system is tipped over. Other structural arrangements that inhibit liquid flow can be incorporated into the conduit such that assembly of the visible valve system to the conduit forms the spill reducing tortuous path. Further, any configuration wherein the breastmilk expression system assembled with the visible valve system forms a spill reducing tortuous path that limits leakage in the system from a container connectable to the breastmilk expression system is within the scope of the present disclosure.

In certain embodiments, the inner valve member is further defined by an interchangeable, visible inner valve member.

In certain embodiments, the visible valve system for a breastmilk expression system includes an externally accessible outer member that can be configured for selective connection to one or both of a conduit and a container. It would be visibly apparent to the user that the outer member is missing or misassembled between the conduit and the container, which advantageously serves to facilitate proper assembly of the various components of the system.

The visible valve system can further include an inner valve member connected to the outer member. The outer member also serves to isolate the inner valve member from external contact and contaminants. For instance, after cleaning of the visible valve system, a user can avoid inadvertently touching the inner valve member.

In certain embodiments, the visible valve system includes an integrally formed inner valve member connected to the outer member. As with other embodiments described herein, it would be visibly apparent to the user that the outer member is missing or misassembled between the conduit and the container.

A visible valve system for a breastmilk expression system of certain embodiments of the present disclosure includes an outer member configured to be grasped by a human hand during use of the breastmilk expression system when selectively assembled in the breastmilk expression system, and an inner valve member connectable to the outer member to a position within a media flow during operation of the breastmilk expression system. The outer member may be larger than the inner valve member, allowing the user to more readily grasp the outer valve member with several fingers, if desired, and place the visible valve system in its intended position during assembly of the breastmilk expression system, while minimizing needed dexterity to place a valve member in its proper location.

DETAILED DESCRIPTION OF THE PREFERRED EMBODIMENTS

Figure 1:
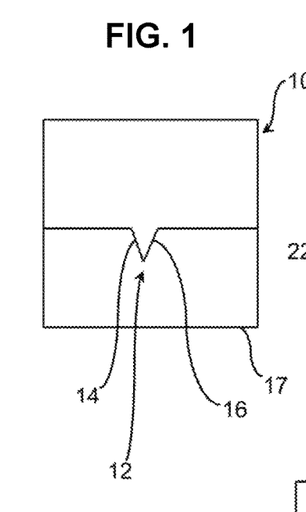
FIG. 1 is a schematic view of a duckbill inner valve for use in a visible valve system constructed in accordance with the principles of the present disclosure, the duckbill inner valve providing selective media communication between a conduit and a container such as a milk collecting container.

As illustrated in FIG. 1, a visible valve system, shown generally at 10, constructed in accordance with the principles of the present disclosure can include a suitable inner valve, or inner valve member, such as an exemplary duckbill inner valve 12. The duckbill inner valve 12 is connected to an outer member 17. The visible valve system 10 is connectable, either directly or indirectly, to an exemplary conduit 40 and an exemplary container 54 (both shown in FIG. 5) of a breastmilk expression system. In an embodiment, the visible valve system 10 can include an outer member 20 that can be disposed between an outer edge of a conduit 40 and a breastmilk collection container 54, and an inner valve selectively connectable to an interior connection section of the outer member 20. The interior connection section can further be disposed within a breastmilk flow path through the valve system. During operation of the breastmilk expression system the conduit can be exposed to varying pressure, such as negative or positive pressure from a pressure source. When negative pressure is applied to the conduit by the pressure source, the flaps 14, 16 of the duckbill inner valve 12 are closed. Upon relieving the negative pressure in the conduit, the flaps 14, 16 of the duckbill inner valve 12 open. This opening of the flaps 14, 16 of the duckbill inner valve 12 brings the conduit into media communication with the container, and breastmilk can flow from the conduit to the container.

Figure 2:
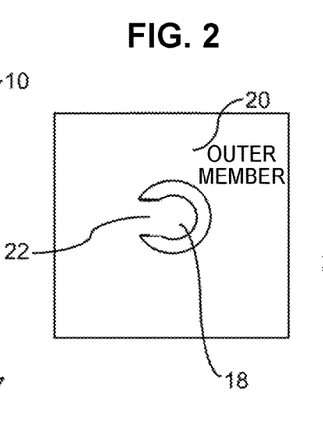
FIG. 2 is a bottom view of a cantilevered flap inner valve for use in a visible valve system constructed in accordance with the principles of the present disclosure.

Turning to FIG. 2, the inner valve may alternately take the form of a cantilevered flap inner valve 18, which may be secured to an outer member 20 by a single joint 22. The outer member 20, the joint 22, and the cantilevered flap inner valve 18 may all be integrally formed of one or more suitable materials, such as an elastomeric material. The joint 22 is sufficiently flexible to permit the cantilevered flap 18 to open due to gravitational forces upon relieving negative pressure in the conduit, yet can be sufficiently rigid to apply a pre-load to the cantilevered flap inner valve 18, such that the cantilevered flap inner valve 18 is biased toward a closed condition.

Figure 3:
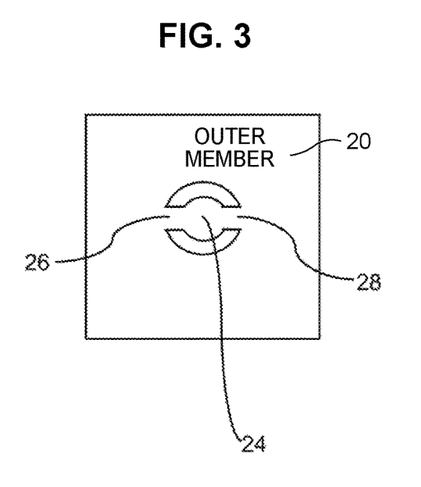
FIG. 3 is a bottom view of an inner valve in the form of a disc-shaped media valve for use in a visible valve system constructed in accordance with the principles of the present disclosure.

FIG. 3 illustrates an inner valve in the form of a disc-shaped media valve 24 that is secured to the outer member 20 by two joints, 26, 28, which are on opposing sides of the inner valve 24. The disc-shaped media valve 24 can be pre-loaded or biased toward a closed condition in sealing engagement with a visible valve seat (as described in more detail below).

Figure 4:
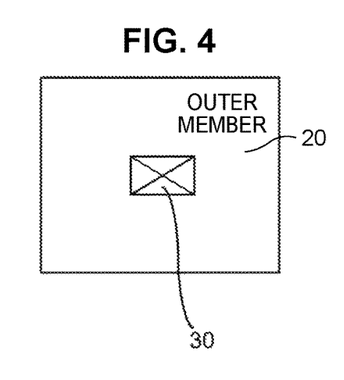
FIG. 4 is a schematic view of an inner valve which may be a suitably-styled inner valve for use in a visible valve system constructed in accordance with the principles of the present disclosure.

FIG. 4 is a schematic diagram depicting a generic inner valve 30 that represents an inner valve of any suitable type that can provide selective media communication between a conduit, such as a milk-receiving cavity of a connector, and a container, such as a milk collecting container. The inner valve can be formed of one or more suitable materials and the outer member can be formed of the same material composition, or a different composition than the inner valve member.

Figures 5, 6, 7:
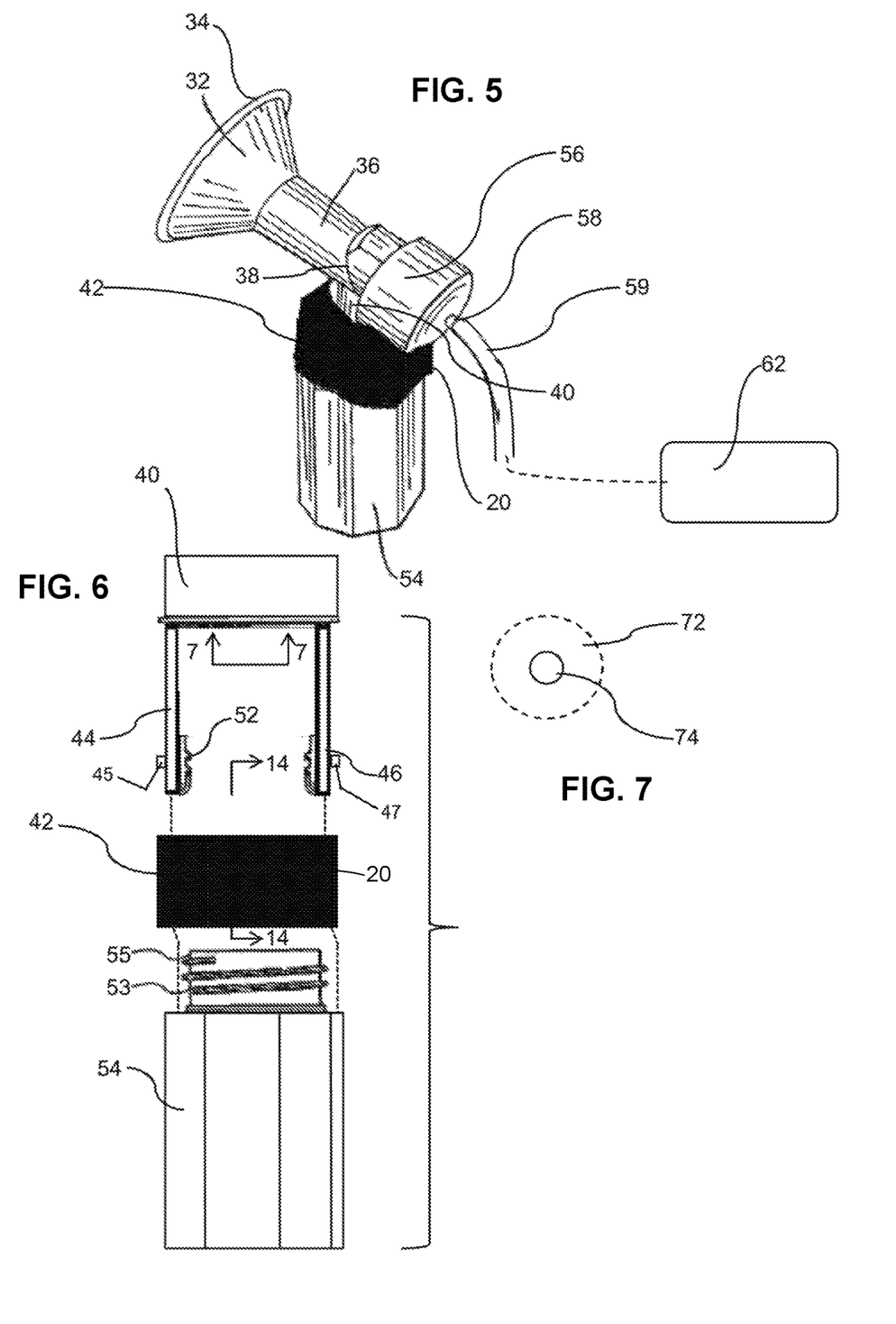
FIG. 5 is a perspective view of a breastmilk expression system having a visible valve system constructed in accordance with the principles of the present disclosure, the visible valve system assembled between a conduit and a container.
FIG. 6 is an exploded view of a visible valve system intermediate a container and an engagement portion of a conduit, the visible valve system configured to detachably fit an outer member to form a substantially continuous connection between a milk collecting container and a conduit.
FIG. 7 is a view taken along lines 7-7 of FIG. 6, illustrating a valve seat of the conduit and an opening therein.
Figure 8:
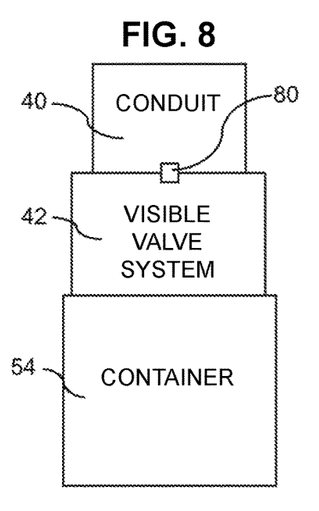
FIG. 8 is a schematic drawing of a conduit, a visible valve system, and a container illustrating a location of a tortuous path to reduce spillage, the tortuous path being in a region where the conduit and visible valve system engage one another.
Figure 9:
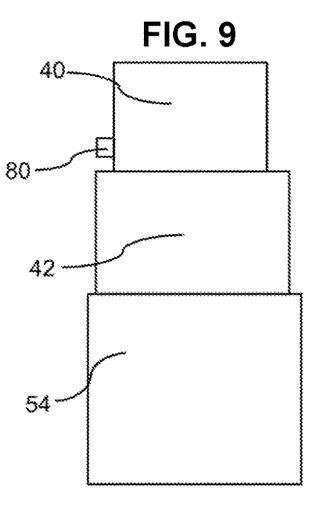
FIG. 9 is a schematic drawing of a conduit, a visible valve system, and a container illustrating a location of a tortuous path to reduce spillage, the tortuous path being part of the conduit.
Figure 10:
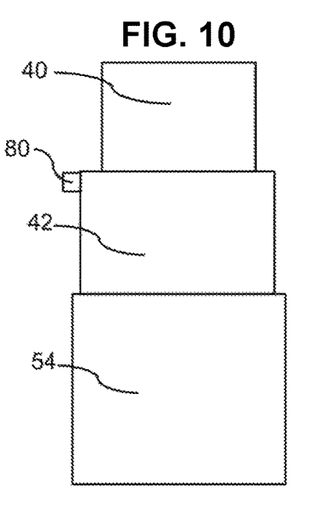
FIG. 10 is a schematic drawing of a conduit, a visible valve system, and a container illustrating a location of a tortuous path to reduce spillage, the tortuous path being part of the visible valve system.
Figure 11:
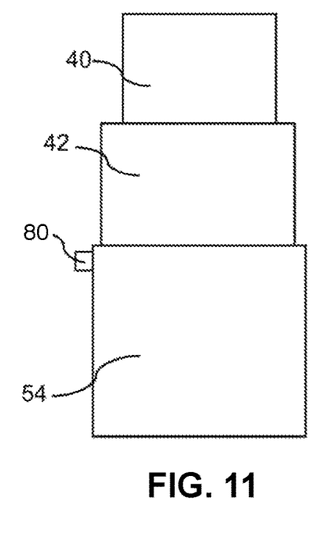
FIG. 11 is a schematic drawing of a conduit, a visible valve system, and a container illustrating a location of a tortuous path to reduce spillage, the tortuous path being part of the container.
Figure 12:
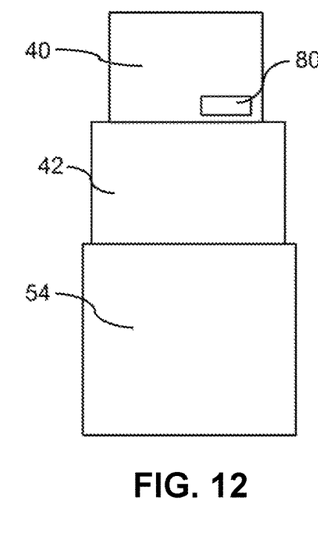
FIG. 12 is a schematic drawing of a conduit, a visible valve system, and a container illustrating a location of a tortuous path to reduce spillage, the tortuous path being within the conduit.
Figure 13:
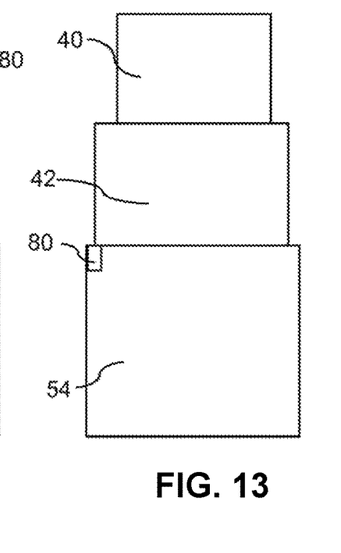
FIG. 13 is a schematic drawing of a conduit, a visible valve system, and a container illustrating a location of a tortuous path to reduce spillage, the tortuous path being part of the container.

Turning to FIG. 5, the visible valve system of the present disclosure is suitable for use in a breastmilk expression system that can include a breastshield assembly. The breastshield assembly, when fully assembled, can include a breastshield 32 having a funnel-shaped first opening 34 and an elongate tubular portion 36 in media communication with the funnel-shaped first opening 34. The elongate tubular portion 36 is received in a complementary aperture 38 of a breastshield adapter or conduit 40, or alternately, the breastshield assembly may be integral with the breastshield adapter or conduit 40. The breastshield adapter or conduit 40 can selectively engage or be fitted to a visible valve system 42.

The visible valve system 42 can include the outer member 20. The breastshield adapter or conduit 40 can include a plurality of downwardly-depending plug elements 44, 46, as best seen in the exploded view of FIG. 6, or can be otherwise configured to secure to the visible valve system 42 via a suitable attachment method. Each of the downwardly-depending plug elements 44, 46 can be configured to be connected to the visible valve system to allow for preassembly of the conduit/valve system. For example, the plug elements 44 can be held, magnetically or otherwise, or received in respective slots of the visible valve system 42, as illustrated by the dotted lines in FIG. 6.

Each of the plug elements 44 of the system may be provided with thread segments 52 that can cooperate with thread segments on the other plug element(s) to threadedly engage a threaded region of the container 54, such as an outer thread 53 of a neck region 55 of a breastmilk collection bottle. Alternatively, the conduit/valve system can be connected to the container via any suitable attachment method, for example magnetic forces or chemical forces.

Further, in an embodiment the downwardly-depending plug elements 44, 46 may be of any suitable shape that facilitates engagement with the outer thread 53 of the neck region 55 of the container 54. For instance, the plug elements 44, 46 may be arcuate. Additionally, any suitable attachment method can be incorporated to secure the conduit to the valve system, such as one or more snap features 45, 47.

In an embodiment shown in FIG. 5, a cap 56 can be secured to a top of the conduit 40. The cap 56 has a port 58 adapted to receive an end of a length of tubing 59 to deliver a pressure from a pressure source 62, such as a pump, to the conduit 40.

As illustrated in FIG. 7, the conduit 40 includes a floor region 72. The floor region 72 can be a suitable shape, such as concave or funnel-shaped, to facilitate the flow of breastmilk temporarily received in the conduit toward a drainage aperture 74 in the floor region 72. It is important to avoid having breastmilk reaching the interior of tubing 59 of FIG. 5 in the system, so that breastmilk does not contaminate the pressure source 62. The fluid media can be separated from the tubing 59 by providing a media separator.

When the breastmilk expression system tips, breastmilk collected in the container 54 thereof tends to flow toward the visible valve system. Where there is a flow path to an exterior of the breastmilk expression system, such as a vent opening, the collected breastmilk could leak through the flow path and out of the breastmilk expression system. As illustrated schematically in FIGS. 8-12, to reduce spilling of milk from the container when the container 54 is tipped over, a leakage limiting member 80 may be either integrally formed in or removably connected to the breastmilk expression system in one or more of a variety of locations, such as on or in the conduit 40, on or in the visible valve system 42, on or in the container 54. Alternately or in addition, the leakage limiting member 80 may be provided intermediate adjacent components, such as intermediate the conduit 40 and the visible valve system 42. The leakage limiting member 80 may be provided on a region of the visible valve system 42 that surrounds the drainage aperture 74.

Figure 14:
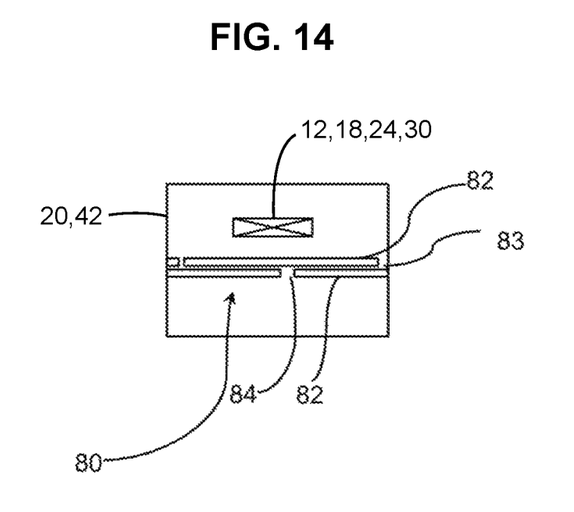
FIG. 14 is a sectional view taken along lines 14-14 of FIG. 6, with the visible valve system including an exemplary embodiment of a spill reducing tortuous path.

As illustrated in FIG. 14, the leakage limiting member 80 may be provided in the visible valve member 42 and may include one or more incomplete ribs 82, if desired. Alternatively, any device for slowing media flow from the container 54 can be provided, and can include one or more devices of any shape or angle for passively providing a spill reducing tortuous path in the system. In addition, FIG. 14 further depicts that the visible valve member 42 may include the outer member 20 and an inner valve member 12, 18, 24, 30. Said another way, the inner valve member may include one or more of the duckbill inner valve 12, the cantilevered flap inner valve 18, the disc-shaped media valve 24, or any other generic inner valve 30.

Where ribs 82 are provided, a gap 84 in each of the incomplete arcuate ribs 82 may be provided at off-set intervals from the gap 84 of adjacent arcuate rib(s) 82. A center-to-center offset of the gaps 84 can be formed at any suitable distance or angle. The arcuate ribs 82 preferably engage an interior wall of the conduit 40 when the conduit 40 and the visible valve system 42 are assembled to one another. The gaps 84 can provide an air path 83 for venting while defining, together with the walls of the arcuate ribs 82, a tortuous path reducing spillage of breastmilk in the event the container topples over.

A tortuous path that reduces spillage of breastmilk may take many forms. A suitable tortuous path may be any structural element, geometric shape, or combination of structural elements or geometry that serves as a flow restrictor, reducing flow rate as media flows past, along, or through the tortuous path. The tortuous path may be disposed closer to the container 54 than the inner valve member when the components of the breastmilk collection system are assembled. Alternately, or additionally, the tortuous path may be disposed more remote from the container 54 than the inner valve member when the components of the breastmilk collection system are assembled.

Figure 17:
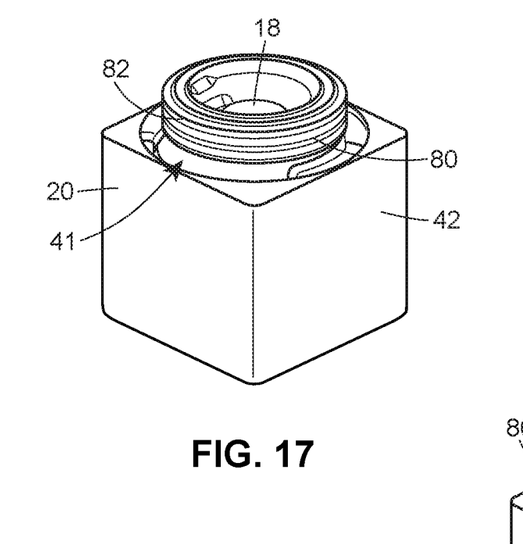
FIG. 17 is a perspective view of the visible valve system constructed in accordance with the principles of the present disclosure and as illustrated in FIGS. 15 and 16.
Figure 18:
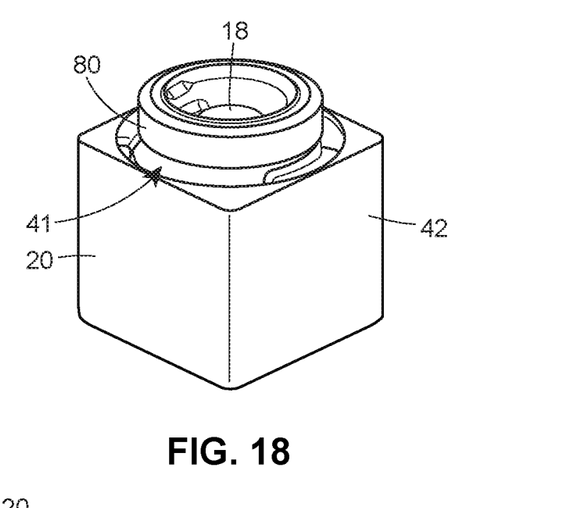
FIG. 18 is a perspective view of the visible valve system constructed in accordance with the principles of the present disclosure and as illustrated in FIGS. 15 and 16, for example, with an alternate example of the visible valve system.

By way of example only, the tortuous path may take the form of a region surrounding the inner valve member that constricts from a first cross-sectional area to a second cross-sectional area that is smaller than the first cross-sectional area more distant from the container 54. Alternately, the tortuous path may take the form of structure surrounding the inner valve member, such as an exemplary neck member 41 that extends from the inner valve member to a position more remote from the container than the inner valve member, as depicted in FIGS. 17 and 18 and explained more below. The tortuous path may also be defined by a first interrupted elongate rib on the neck member 41 and a second interrupted rib on the neck member 41 spaced from the first interrupted rib by a channel, an interruption of the first interrupted elongate rib being offset from an interruption of the second interrupted elongate rib.

Figure 15:
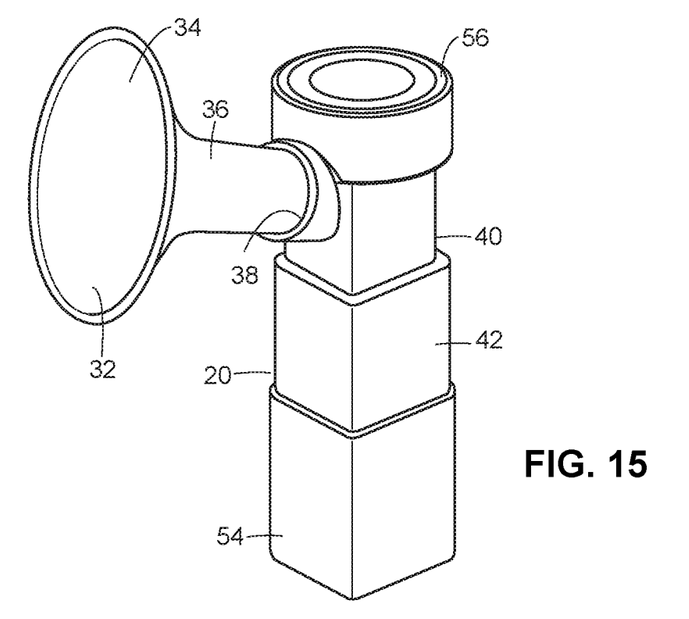
FIG. 15 is a front perspective view of the breastmilk expression system having the visible valve system constructed in accordance with the principles of the present disclosure, the visible valve system assembled between the conduit and the container.
Figure 16:
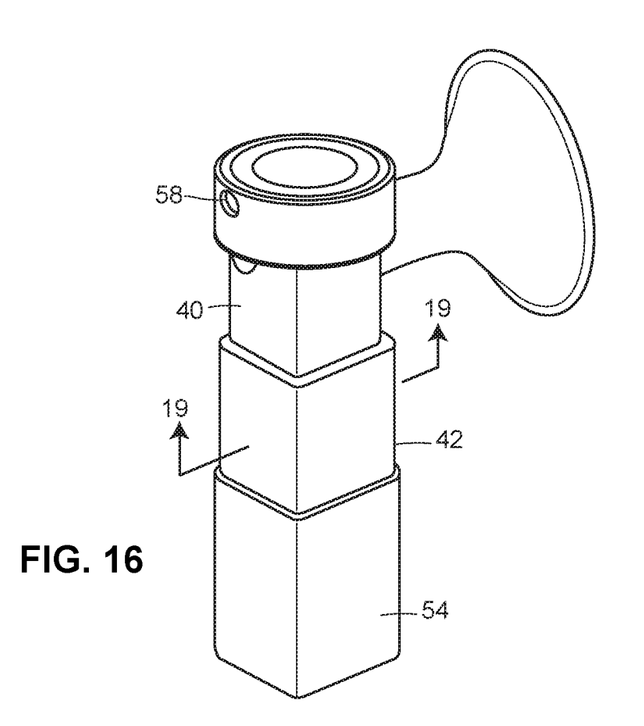
FIG. 16 is a rear perspective view of the breastmilk expression system of FIG. 15.

Referring now to FIGS. 15 and 16, and like FIGS. 5 and 6, the visible valve system of FIGS. 15 and 16 is suitable for use in a breastmilk expression system that can include the breast shield assembly. The breast shield assembly, when assembled, can include the breast shield 32 having the funnel-shaped first opening 34 and the elongate tubular portion 36, which is received in the complementary aperture 38 of the breast shield adapter or conduit 40. Alternatively, the breast shield assembly may be integral with the breast shield adapter or conduit 40, which may selectively engage or be fitted to the visible valve system 42. As noted, the visible valve system 42 can include the outer member 20 and may engage the container 54. In addition, the cap 56 may be secured to the top of the conduit 40. The cap 56 has a port 58 (FIG. 16), which is adapted to receive the end of a length of tubing 59 to deliver a pressure from the pressure source 62 (FIG. 5), such as a pump, to the conduit 40.

As one of ordinary skill in the art will appreciate, each of the conduit 40, the visible valve system 42, the container 54, and the cap 56 may take the form of various different shapes and still fall within the scope of the present disclosure. For example, and as depicted in FIGS. 15 and 16, each of the conduit 40, the visible valve system 42, and the container 54 may be cube-like or square in shape. In addition, the cap 56 may be cylindrical in shape. In another example, and as depicted in FIGS. 5 and 6, the container 54 may be more hexagonal or orthogonal in shape, and the conduit 40 may be more cylindrical in shape.

Referring now to FIGS. 17 and 18, the leakage limiting member 80 may be provided on a region of the visible valve system 42, such as the neck region. In one example, the leakage limiting member 80 may extend upwardly. In another example, the leakage limiting member 80 may be provided in the visible valve member 42 and may include one or more ribs 82. Alternatively, the leakage limiting member 80 may not include any ribs 82, as depicted in FIG. 18.

Figure 19:
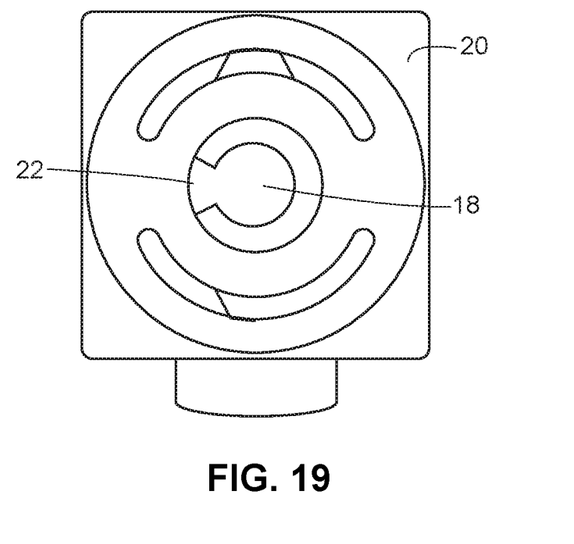
FIG. 19 is a bottom view of the breastmilk expression system of FIG. 16, taken along the line 19-19 of FIG. 16, wherein a visible valve system constructed in accordance with the principles of the present disclosure includes a cantilevered flap inner valve of the type depicted in FIG. 2.

Referring now to FIG. 19, a bottom view of the breastmilk expression system of FIG. 16, taken along the line 19-19 of FIG. 16 is depicted. In this example, the visible valve system 42 includes the outer member 20 and the cantilevered flap inner valve 18, as also depicted in FIG. 2. The cantilevered flap inner valve 18 is secured to the outer member 20 by the joint 22. As described above relative to FIG. 2, for example, the outer member 20, the joint 22, and the cantilevered flap inner valve 18 may all be integrally formed of a suitable material, such as elastomeric material.

Referring again to FIGS. 6, 7, 15, 16 and 19, once conduit 40 and visible valve system 42 are assembled, the inner valve, such as the cantilevered flap inner valve 18, aligns with the drainage aperture 74, sealingly engaging the underside of the floor region 72 of the conduit 40, which serves as a valve seat to the visible valve system.

The visible valve system of the present disclosure can provide a convenient reminder to the user that the breastmilk collection system has been properly assembled. This is due to the fact that if the visible valve system is missing and the user attempts to connect the conduit 40 directly to the container 54, there can be a gap between the conduit 40 and the container 54. In other words, the visible valve system can serve as an outer member that is externally accessible. The outer member is configured to selectively connect to both the conduit 40, and to the container 54. It is visibly apparent to the user if the outer member 20 is missing or misassembled between the conduit 40 and the container 54 since the outer member 20 is sufficiently sized to form a visible, substantially continuous connection between the conduit 40 and the container 54.

In an embodiment, the breastmilk expression system may be constructed in such a manner that the container 54 cannot be assembled with the rest of the system if the visible valve system is not included. As such, the visible valve system serves as a necessary connecting portion, even if the mechanism for securing the container 54 to the breastmilk expression system, such as the thread segments 52 of the plug elements 44, 46, is provided as part of a different component than the visible valve system 42, like the breastshield adapter or conduit 40, for example.

The visible valve system of the present disclosure also provides a convenient location for grasping by a human hand during use of the breastmilk expression system, due to the substantially continuous connection between the conduit and the container formed when the breastmilk expression system is properly assembled. When so assembled, the user is assured that a visible valve system is properly provided between a conduit and a container so that upon application of a pressure to the conduit, the visible valve system will be retained in a sealed condition, and upon release or relaxation of the pressure, the visible valve system will open. Upon application of the pressure, with a breastshield of the breastmilk expression system applied to the breast, breastmilk will be temporarily collected in the conduit. Upon release or relaxation of the negative pressure, the visible valve system will open, resulting in the breastmilk flowing from the conduit to the container via the visible valve system.

In accordance with the principles herein, an exemplary method of reducing spillage for a breastmilk expression system can include the following steps: First, a breastmilk collection kit having a conduit, a container and a valve is produced. The valve can include an inner valve member through which media can flow into a container and an outer member connected to the inner valve member. The outer member can include a spill-reducing tortuous path. Next, the outer member can be configured to be connectable to the container so that the system is capable of reducing a flow rate in the container.

Producing the breastmilk collection kit can further include at least one of the following steps: (1) providing a constriction from a first cross-sectional area to a second cross-sectional area that is smaller than the first cross-sectional area more distant from the container; and (2) providing a vent having a neck member that extends from the inner valve member to a position more remote from the container than the inner valve member, wherein either step results in a breastmilk collection kit that reduces the flow rate in the container during use.

In accordance with the principles herein, a breastmilk expression system can include a visible valve system connectable, either directly or indirectly, to one or more of a conduit and a container; an inner valve member connected to the visible valve system; and a spill-reducing tortuous path one or more of integrally formed in or removably connected to one or more of: on or in the container, on or in the conduit, on or in the visible valve system, intermediate the conduit and the visible valve system, and intermediate the container and the visible valve system.

The visible valve system can further include an outer member of the valve.

In an embodiment, the breastmilk expression system can further include a leakage limiting member, the leaking limiting member including the spill-reducing tortuous path.

As one of ordinary skill in the art will understand, any breastmilk referred to in the foregoing disclosure, such as in reference to the breastmilk expression system, is breastmilk from a human, e.g., a human mother, and not any other mammal or species. For example, the breastmilk expression system of the present disclosure is directed to expressing breastmilk from a human mother.

While the present disclosure has been described with respect to certain embodiments thereof, combinations and variations of the disclosed embodiments may be implemented that are still within the scope of the appended claims.

What is claimed is:

1. A valve system connectable to a container of a breastmilk expression system comprising:
    an inner valve member through which a media can flow into the container; and
    an outer member connected to the inner valve member, the outer member including a spill-reducing tortuous path, the spill-reducing tortuous path including means for reducing flow rate,
    wherein the means for reducing flow rate includes a first interrupted elongate rib having an opening in the first interrupted elongate rib and a second interrupted elongate rib adjacent to the first interrupted elongate rib and having an opening in the second interrupted elongate rib, a distance between the openings comprises a first distance between the first and second interrupted elongate ribs and a second distance along the first and second interrupted elongate ribs, the opening in the first interrupted elongate rib is provided at an offset interval from the opening in the second interrupted elongate rib, the openings defining, together with walls of the first and second interrupted elongate ribs, the spill-reducing tortuous path, and
    wherein the outer member is directly visible from an exterior of the breastmilk expression system when the breastmilk expression system is assembled, and the outer member includes a first end and a second end disposed opposite to the first end, the first end adapted to be removably attached to a conduit and the second end adapted to be attached to the container.

2. The valve system of claim 1, wherein the spill-reducing tortuous path is at least partially defined by the container.

3. The valve system of claim 1, wherein the means for reducing flow rate includes an airpath for venting.

4. The valve system of claim 1, wherein the means for reducing flow rate includes a neck member that extends from the inner valve member.

5. The valve system of claim 4, wherein the means for reducing flow rate includes the first interrupted elongate rib and the second interrupted rib spaced from the first interrupted elongate rib by a channel.

6. A breastmilk expression system having a valve system connectable to a container as set forth in claim 1, further comprising a conduit configured for connection to the valve system, and a breastshield configured for connection to the conduit.

7. The breastmilk expression system of claim 6, the valve system further defined by the outer member sufficiently sized to form a visible, substantially continuous connection between the conduit and the container, the outer member being externally accessible and configured to connect to both the conduit and the container.

* * * * *